United States Patent
Burnes et al.

(10) Patent No.: US 10,743,779 B2
(45) Date of Patent: Aug. 18, 2020

(54) MONITORING MODE OF AN IMPLANTABLE MEDICAL DEVICE

(71) Applicant: Medtronic, Inc., Minneapolis, MN (US)

(72) Inventors: John Burnes, Coon Rapids, MN (US); Rebecca Poindexter, Minneapolis, MN (US); Daniel Bloomberg, Minneapolis, MN (US); Christopher M. Hobot, Rogers, MN (US); Roland C. Maude-Griffin, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 257 days.

(21) Appl. No.: 15/547,607

(22) PCT Filed: Feb. 2, 2016

(86) PCT No.: PCT/US2016/016077
§ 371 (c)(1),
(2) Date: Jul. 31, 2017

(87) PCT Pub. No.: WO2016/126648
PCT Pub. Date: Aug. 11, 2016

(65) Prior Publication Data
US 2018/0263511 A1   Sep. 20, 2018

Related U.S. Application Data (60) Provisional application No. 62/111,355, filed on Feb. 3, 2015.

(51) Int. Cl.
*A61B 5/0205* (2006.01)
*A61B 5/11* (2006.01)
(Continued)

(52) U.S. Cl.
CPC .......... *A61B 5/02055* (2013.01); *A61B 5/002* (2013.01); *A61B 5/0464* (2013.01);
(Continued)

(58) Field of Classification Search
CPC . A61B 5/02055; A61B 5/002; A61B 5/14546; A61B 5/1116; A61B 5/686;
(Continued)

(56) References Cited

U.S. PATENT DOCUMENTS 8,246,563 B2    8/2012  Wariar
9,398,853 B2 *  7/2016  Nanikashvili .......... A61B 5/002
(Continued)

FOREIGN PATENT DOCUMENTS

EP         2719406 B1      5/2016
WO    WO2013022760 A1     8/2011

OTHER PUBLICATIONS

International Search Report for PCT/US2016/016077 date of completion is May 9, 2016 (three pages).
EP OA for App. No. 16709165.1 dated Oct. 22, 2019.

*Primary Examiner* — Leslie R Deak
(74) *Attorney, Agent, or Firm* — Hahn & Associates (57) ABSTRACT

A system and method for controlling a monitoring mode or treatment mode of an implantable medical device based on the detection of an external signal. The system and related method allow for more frequent monitoring of medical parameters at times where more frequent monitoring is necessary, such as during or after a dialysis session, with less frequent monitoring at other times, allowing for a more efficient medical device. The invention also allows for the frequency or mode of treatment by the implantable medical device, or the transmission of data from the implantable medical device to be controlled based on the external signal.

20 Claims, 3 Drawing Sheets

(51) Int. Cl.
    *A61B 5/145*     (2006.01)
    *A61M 1/36*     (2006.01)
    *A61B 5/00*     (2006.01)
    *A61B 5/20*     (2006.01)
    *G16H 40/63*     (2018.01)
    *A61M 1/16*     (2006.01)
    *A61M 16/00*     (2006.01)
    *A61B 5/0464*     (2006.01)
    *A61B 5/021*     (2006.01)
    *A61B 5/024*     (2006.01)
    *A61B 5/08*     (2006.01)
    *A61B 5/01*     (2006.01)
    *A61B 5/0402*     (2006.01)
    *A61B 5/0245*     (2006.01)
    *A61B 5/053*     (2006.01)
    *G06F 19/00*     (2018.01)
    *A61N 1/37*     (2006.01)
    *A61N 1/39*     (2006.01)

(52) U.S. Cl.
CPC ........... *A61B 5/1116* (2013.01); *A61B 5/1118* (2013.01); *A61B 5/14532* (2013.01); *A61B 5/14535* (2013.01); *A61B 5/14546* (2013.01); *A61B 5/201* (2013.01); *A61B 5/4875* (2013.01); *A61B 5/686* (2013.01); *A61B 5/746* (2013.01); *A61M 1/1605* (2014.02); *A61M 1/3609* (2014.02); *A61M 16/0051* (2013.01); *A61M 16/024* (2017.08); *G06F 19/00* (2013.01); *G16H 40/63* (2018.01); *A61B 5/01* (2013.01); *A61B 5/021* (2013.01); *A61B 5/024* (2013.01); *A61B 5/0245* (2013.01); *A61B 5/02405* (2013.01); *A61B 5/0402* (2013.01); *A61B 5/053* (2013.01); *A61B 5/0816* (2013.01); *A61B 5/14542* (2013.01); *A61B 5/4836* (2013.01); *A61B 2560/029* (2013.01); *A61B 2560/0209* (2013.01); *A61B 2562/0257* (2013.01); *A61M 2205/04* (2013.01); *A61M 2205/3303* (2013.01); *A61M 2205/3324* (2013.01); *A61M 2205/3368* (2013.01); *A61M 2205/3523* (2013.01); *A61M 2205/3569* (2013.01); *A61M 2230/201* (2013.01); *A61M 2230/202* (2013.01); *A61M 2230/205* (2013.01); *A61M 2230/207* (2013.01); *A61M 2230/30* (2013.01); *A61M 2230/40* (2013.01); *A61N 1/3704* (2013.01); *A61N 1/3925* (2013.01); *A63B 2230/04* (2013.01)

(58) Field of Classification Search
CPC ............. A61B 5/1118; A61B 5/14532; A61B 5/14535; A61B 5/201; A61B 2562/0257; A61B 5/0245; A61B 5/14542; A61B 2560/029; A61B 5/053; A61B 2560/0209; A61B 5/0402; A61B 5/4836; A61B 5/02405; A61B 5/021; A61B 5/0816; A61B 5/024; A61B 5/01; A61B 5/0464; A61B 5/4875; A61B 5/746; A63B 24/0062; A63B 22/02; A63B 2230/04; G06F 19/00; G16H 40/63; A61M 1/3609; A61M 2230/205; A61M 2205/3368; A61M 2205/3324; A61M 2205/3303; A61M 2230/40; A61M 2230/201; A61M 2230/202; A61M 2230/207; A61M 2205/04; A61M 2230/30; A61M 2205/3569; A61M 2205/3523; A61M 1/1605; A61M 16/024; A61M 16/0051; A61M 1/14; A61N 1/3704; A61N 1/3925
See application file for complete search history.

(56) References Cited

U.S. PATENT DOCUMENTS

2003/0032993 A1\*   2/2003   Mickle ................ G06K 7/0008
                                                                           607/60
2007/0175827 A1   8/2007   Wariar \* cited by examiner

MONITORING MODE OF AN IMPLANTABLE MEDICAL DEVICE

CROSS-REFERENCE TO RELATED APPLICATIONS

This application is a National Stage Application of PCT/US2016/016077 under 35USC § 371 (a), which claims benefit of and priority to U.S. Provisional Patent Application Ser. No. 62/111,355 filed Feb. 3, 2015, the disclosures of each of the above-identified applications are hereby incorporated by reference in their entirety.

FIELD OF THE INVENTION

The invention relates to systems and methods for monitoring medical parameters by an Implantable Medical Device (IMD). The IMD is capable of switching a mode of monitoring the medical parameters based on an external trigger generated from an external medical device. The systems and methods encompass any medical therapy that can collect data from an IMD to assist in therapy goals. Non-limiting exemplary therapies include cardiovascular therapy and dialysis, among others.

BACKGROUND

Implantable Medical Devices (IMDs) enable constant monitoring of a patient's health, and delivery of therapy to the patient, while allowing freedom of movement and portability not possible with external monitoring devices. IMDs are limited by the life of the battery that powers the IMD. Once the battery within an IMD has reached the end of the battery's useful life, a new battery or device must be installed. Because the IMD is implanted into a patient, installation of a new battery or device requires an invasive and expensive medical procedure, subjecting the patient to the risks of an additional procedure.

IMDs are commonly used in patients with Chronic Kidney Disease (CKD). In addition to providing therapy to a patient suffering from CKD, the IMDs can monitor the patient's health. However, known IMDs do not selectively monitor a patient's health status, such as fluid status, electrolyte concentration, and arrhythmias based on proximity relative to external medical devices.

Known IMDs do not allow for automatic changes in the mode or frequency of medical monitoring in the time periods during or immediately after dialysis. Known IMDs also do not allow for the IMD to automatically switch between modes that place a high stress on battery life and modes that place a low stress on battery life based on whether or not a dialysis session is occurring or has just occurred.

Hence, there is a need for an IMD that can automatically switch monitoring modes at the initiation of a medical therapy, for example, at start of a dialysis session, and switch monitoring modes again at some point after the initiation of the medical therapy. There is further a need for an IMD that can conserve battery life during the time periods between a medical therapy, such as a dialysis session, while automatically switching to more thorough monitoring during and immediately after a medical therapy, increasing longevity of the IMD. There is a further need for an IMD that can change monitoring modes when the IMD is within range of an external monitor or memory component capable of receiving data. There is also a need for an IMD that can change treatment modes based on external factors, such as the start of a medical therapy, such as a dialysis session.

SUMMARY OF THE INVENTION

The first aspect of the invention relates to a medical monitoring system. In any embodiment of the first aspect of the invention, the medical monitoring system can comprise an implantable medical device having one or more sensors configured to monitor data corresponding to at least one medical parameter; an input in electronic communication with the implantable medical device, wherein the input is configured to receive a signal corresponding to at least one trigger; and an external medical device configured to transmit the signal to the implantable medical device; wherein the implantable medical device is configured to change a mode of monitoring the at least one medical parameter or of treating a medical condition associated with the at least one medical parameter based on the signal corresponding to the at least one trigger.

In any embodiment of the first aspect of the invention, the mode of monitoring the at least one medical parameter or of treating the medical condition associated with at least one medical parameter can be changed from a first mode to a second mode in response to the signal corresponding to at least one trigger. The first mode can be selected from a high resolution, a low resolution, a real-time, a transmission mode, an on mode, an off mode, a non-inhibited mode, an alert mode, a high threshold mode, and a low threshold mode, and the second mode can be any one of a high resolution, a low resolution, a real-time, a transmission mode, an on mode, an off mode, a non-inhibited mode, an alert mode, a high threshold mode, and a low threshold mode.

In any embodiment of the first aspect of the invention, the system can further comprise a monitor in wireless communication with the implantable medical device, wherein the monitor is configured to receive and display the data corresponding to the monitored medical parameter.

In any embodiment of the first aspect of the invention, the implantable medical device can be configured to transmit the data to the external medical device, and the external medical device can be configured to receive the data.

In any embodiment of the first aspect of the invention, the external medical device can be a dialysis machine.

In any embodiment of the first aspect of the invention, the dialysis machine can automatically set at least one dialysis parameter based on the received data.

In any embodiment of the first aspect of the invention, the external medical device can be a medical monitor, and in response to the trigger the implantable medical device can enter a transmission mode.

In any embodiment of the first aspect of the invention, the medical monitoring system can further comprise a memory component in communication with the implantable medical device; wherein the implantable medical device is configured to transmit the data to the memory component; and wherein the memory component is configured to receive and record the data.

In any embodiment of the first aspect of the invention, the memory component can be a non-transitory recording medium.

In any embodiment of the first aspect of the invention, the memory component can be part of the implantable medical device.

In any embodiment of the first aspect of the invention, the at least one medical parameter can be selected from the group comprising impedance, fluid status indicators, ECG, EGM, heart rate, heart rate variability, blood pressure, patient activity level, glucose level, potassium level, calcium level, magnesium level, sodium level, hematocrit level, urea level, $CO_2$ level, respiration, patient posture, and patient temperature.

In any embodiment of the first aspect of the invention, the mode of monitoring the at least one medical parameter can initiate monitoring of a medical parameter or terminate the monitoring of a medical parameter.

In any embodiment of the first aspect of the invention, the external medical device can be selected from any one of a dialysis machine, an external monitor, a scale, a blood pressure monitoring system, a monitor, a nurse monitoring system, a computer having an electronic medical record, a CPAP machine, an exercise equipment, and a physiologic monitoring device.

In any embodiment of the first aspect of the invention, the trigger can be proximity to the external medical device.

In any embodiment of the first aspect of the invention, the implantable medical device can automatically receive the signal from the external medical device.

In any embodiment of the first aspect of the invention, the implantable medical device can be configure to any of (i) always be capable of detecting the trigger; (ii) be capable of detecting the trigger at a set time; (iii) be capable of detecting the trigger at a set frequency, and/or (iv) be configured such that a user can cause the implantable medical device to become capable of detecting the trigger.

In any embodiment of the first aspect of the invention, the implantable medical device is enclosed with another medical device.

Any of the features described as being part of the first aspect of the invention can be included in the first aspect of the invention, either alone or in combination.

The second aspect of the invention relates to a method of controlling the monitoring mode of an implantable medical device. In any embodiment of the second aspect of the invention, the method can comprise the steps of establishing a wireless communication between an external medical setting and an implantable medical device; receiving a trigger from the external medical setting to the implantable medical device; and switching from a first data collection mode to a second data collection mode in the implantable medical device based on the trigger.

In any embodiment of the second aspect of the invention, the trigger can be any one of proximity to the external medical setting, an external communication message, a user trigger, or an algorithmic trigger.

In any embodiment of the second aspect of the invention, the method can further comprise the step of transmitting data, control instructions, alerts, triggers, or programming between the external medical setting and the implantable medical device via the wireless link.

In any embodiment of the second aspect of the invention, the first data collection mode can be any one of a high resolution mode, a low resolution mode, a real-time mode, a transmission mode, an on mode, an off mode, a non-inhibited mode, an alert mode, a high power consumption mode, a low power consumption mode, a high threshold mode, and a low threshold mode, and wherein the second data collection mode can be any one of a high resolution mode, a low resolution mode, a real-time mode, a transmission mode, an on mode, an off mode, a non-inhibited mode, an alert mode, a high power consumption mode, a low power consumption mode, a high threshold mode, and a low threshold mode.

In any embodiment of the second aspect of the invention, the data can include parameters for any one of impedance, fluid status indicators, ECG or EGM, heart rate, heart rate variability, blood pressure, patient activity, glucose level, potassium level, calcium level, magnesium level, sodium level, hematocrit level, urea level, $CO_2$ level, respiration, patient posture, patient temperature, and arrhythmia status.

In any embodiment of the second aspect of the invention, the external medical setting can be selected from any one of a dialysis machine, an external monitor, a scale, a blood pressure measurement system, a monitor, a nurse monitoring system, a computer having an electronic medical record, a CPAP machine, an exercise equipment, and a physiologic monitoring device.

In any embodiment of the second aspect of the invention, the method can further comprise switching from the second monitoring mode to the first monitoring mode after a set period of time after receiving the trigger.

In any embodiment of the second aspect of the invention, the method can comprise switching from the second monitoring mode to the first monitoring mode after receiving a second trigger.

Any of the features described as being part of the second aspect of the invention can be included in the second aspect of the invention, either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "activity" or "activity level" as used herein refers to the amount of physical activity of a patient.

An "algorithmic trigger" is a trigger, wherein in response to the value of some parameter, the device receiving the algorithmic trigger takes an action of any type.

An "alert mode" refers to a mode of monitoring a medical parameter with a monitor than can deliver therapy wherein the monitor provides an alert in response to a medical parameter crossing a predetermined threshold, but does not automatically provide therapy in response to the medical parameter crossing a predetermined threshold.

The term "CPAP machine" refers to a device that provides continuous positive airway pressure to a subject. The device uses positive air pressure to keep the airways of the subject open and improve the breathing ability of the subject.

The terms "communicate" and "communication" include but are not limited to, the connection between the electrical elements of the system, either directly or wirelessly, using optical, electromagnetic, electrical, acoustic or mechanical connections, for data transmission among and between said elements.

The term "comprising" includes, but is not limited to, whatever follows the word "comprising." Use of the term indicates the listed elements are required or mandatory but that other elements are optional and may or may not be present.

The term "consisting of" includes and is limited to whatever follows the phrase the phrase "consisting of." The phrase indicates the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

The terms "data collection mode" and "monitoring mode" refer to the method of data collection or monitoring of a medical device. As used herein, data collection modes or monitoring modes include but are not limited to: the frequency of measurements, the resolution of measurements, whether specific medical parameters are monitored, or the whether certain data is transmitted to a receiver.

A "dialysis parameter" is any factor of a dialysis session that tends to affect the health of the patient during and after dialysis. As used herein, "dialysis parameter" includes, but is not limited to, occurrence of dialysis, fluid removal prescription such as a "dialysis session prescription," fluid removal rate, electrolyte balance of the dialysate or pH of the dialysate.

The term "display" as used herein means presentation of information on a computer screen of any type or form.

The term "enclosed within another medical device" refers to a device or system that is part of, or housed within, a larger device, and not a stand alone piece of equipment.

"Exercise Equipment" refers to any piece of equipment generally used for physical activity by a subject. Non-limiting examples of exercise equipment include treadmills, elliptical equipment, or stair climbers.

An "external communication message" is a transmission received from a source external to a system.

An "external medical device" describes any device, component or module that is outside of a patient's body. An external medical device can refer, but is not limited to, any treatment device, monitoring device, or physiological data recording device.

An "external medical setting" refers to any device, location, or structure outside of a patient's body. An external medical setting can refer to a particular external medical device, a hospital, a clinic, or any other setting.

"Fluid status indicators" are any parameters that tend to indicate the fluid status of a patient. Changes in fluid status indicators are proportional to changes in the fluid levels of the patient.

A "high power consumption mode" refers to a mode of monitoring a medical parameter with a medical device, wherein the medical device is configured to use more power than in the normal operating conditions. The higher power consumption can be based on an increased frequency of monitoring, an increased frequency of transmission, an increased frequency of treatment, or any other factors that would tend to increase the power requirements of the medical device.

A "high resolution mode" refers to a mode of monitoring a medical parameter wherein data concerning the medical parameter is sensed or transmitted intermittently, but at a high frequency. There is no set amount of time between sensing or transmission of the data to be considered "high resolution," however, in a high resolution mode the sensing or transmission will occur with a frequency that is greater than when the monitor is not in a high resolution mode.

A "high threshold mode" refers to a mode of monitoring a medical parameter wherein the threshold for detecting a medical event or delivering therapy in response to the medical parameter is set to a higher limit.

The term "implantable medical device" describes a device, component or module intended to be totally or partially introduced, surgically or medically into a mammalian body, or by medical intervention that remains after the procedure.

An "input" as used herein is a component that allows data to be entered into or received by a device or system. The input can provision the submission of data of any type for further processing by the device or system.

A "low power consumption mode" refers to a mode of monitoring a medical parameter with a medical device, wherein the medical device is configured to use less power than in the normal operating conditions. The lower power consumption can be based on a reduced frequency of monitoring, a reduced frequency of transmission, a reduced frequency of treatment, or any other factors that would tend to decrease the power requirements of the medical device.

A "low resolution mode" refers to a mode of monitoring a medical parameter wherein data concerning the medical parameter is sensed or transmitted intermittently. There is no set amount of time between sensing or transmission of the data to be considered "low resolution," however, in a low resolution mode the sensing or transmission will occur less often than the monitor is capable of sensing or transmitting the data.

A "low threshold mode" refers to a mode of monitoring a medical parameter wherein the threshold for detecting a medical event or delivering therapy in response to the medical parameter is set to a lower value of any type relative to another value.

A "medical monitoring system" is a system including one or more sensors that are configured to sense at least one medical parameter of a patient.

A "medical parameter" is any data that gives information about the health of a patient. As used herein, the term "medical parameter" includes, but is not limited to electromyogram (EMG), an electroencephalogram (EEG), an electrocardiogram (ECG), tissue impedance, blood pressure, the level of specific ions in the blood of a patient such as, but not limited to potassium, sodium, and calcium, patient weight including both dry weight and wet weight, pre- and post-dialysis, a fluid profile including current and historical profiles, or other data concerning the health of the patient such as arrhythmia information, heart rate, fluid level, and blood ion levels.

A "memory component" is a component capable of recording and saving data.

A "medical condition associated with a medical parameter," as used herein, refers to a health state of a patient, wherein the health state can be determined, at least in part, based on the medical parameter.

The term "mode of monitoring," as used herein, describes the operating parameters of a medical device, such as the frequency or resolution of data collection.

A "non-inhibited mode" refers to a mode of delivering therapy with an implantable medical device, wherein the therapy is delivered independently of detection of medical parameters as defined herein.

An "off mode" refers to a monitor that is not currently monitoring a particular medical parameter.

An "on mode" refers to a mode of monitoring a medical parameter wherein the monitor is actively monitoring the medical parameter.

A "patient" is a member of any animal species, preferably a mammalian species, optionally a human. The subject can be an apparently healthy individual, an individual suffering from a disease, or an individual being treated for an acute condition or a chronic disease.

The term "posture" as used herein refers to the body positioning of a patient.

A "physiologic monitoring device" is an external medical device capable of sensing data regarding one or more medical parameters of a patient.

The term "proximity" refers to the distance between two objects.

The term "signal" refers to a transitory or non-transitory transmission.

A "real time mode" refers to a mode of monitoring a medical parameter wherein data concerning the medical parameter is sensed or transmitted constantly, or nearly constantly.

A "sensor" is a device capable of measuring at least one parameter of a system or patient.

The term "switching," as used herein, refers to changing the mode of a medical device or sensor.

A "transmission mode" refers to a mode of monitoring a medical parameter wherein the data concerning the medical parameter is communicated to a receiver.

A "trigger" is a signal that causes a device receiving the signal to take an action of any type.

A "user trigger" is a signal that is directed by a human user and that causes device receiving the signal to take an action of any type.

Medical Monitoring System

Because of the changes in several medical parameters that occur during a dialysis or other kidney treatment session, this monitoring becomes especially important in the time period immediately before, during and after a kidney treatment session. The type of data that should be monitored in the time periods during and immediately after a dialysis session can be different from the types of data that are commonly monitored between dialysis sessions. Further, the frequency of the need for monitoring can also change during or immediately after a dialysis session. Additionally, the level of resolution necessary for effective monitoring can increase during or after a dialysis session.

In addition to providing therapy, IMDs can perform a range of medical monitoring functions. Non-limiting examples of medical parameters that can be monitored by the IMDs of the present invention include impedance, fluid status, ECG, EGM, heart rate, heart rate variability, blood pressure, hematocrit levels, glucose levels, potassium or other electrolyte levels, patient activity levels, patient posture, respiration, $CO_2$ levels, and body temperature. In some situations, the frequency of measurements of medical parameters does not need to be as often as in other situations. One advantage of the first and second aspects of the invention is that the frequency of monitoring some or all of the medical parameters can be increased in situations where there is a greater need for monitoring, thus conserving battery life. Another advantage is that the first and second aspects of the invention also contemplate one or more of the sensing functions performed by the IMD being taken over by external sensors during in-clinic dialysis to conserve battery. The type of sensing can be dependent on the particular need wherein a specially adapted computer or processor can determine whether the IMD is required to have all, some, or none of the sensing functions active during dialysis. For example, ECG data can be collected by external sensors during dialysis, thus relieving ECG function from the IMD. Similarly, heart rate and blood pressure measurements obtained by an IMD inter-session can be relieved by in-clinic data collection and monitoring devices during dialysis.

However, known IMDs do not selectively monitor a patient's health status, such as fluid status, electrolyte concentration, and arrhythmias based on external factors such as the occurrence of dialysis. Selectively monitoring a patient's health status can provide life saving information to the patient and health care providers.

Figure 1:
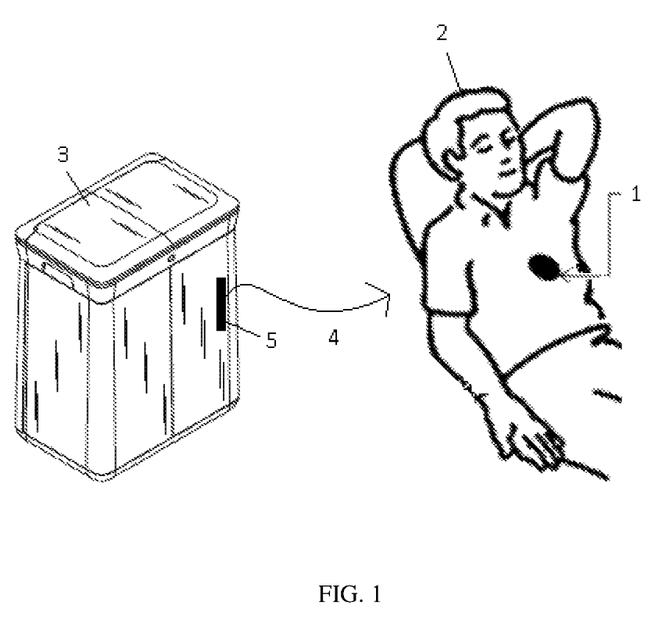
FIG. 1 is a medical monitoring system according to an embodiment wherein the external trigger source is a dialysis machine.

FIG. 1 shows a non-limiting embodiment of the first and second aspects of the invention. A medical device 1 with monitoring capabilities can be implanted in a patient 2. Upon receiving a trigger signal 4 from a transmitter 5 on an external setting, such as dialysis machine 3, the IMD can automatically switch monitoring modes. In any embodiment of the first and second aspects of the invention, as shown in FIG. 1, the trigger can be based on the proximity of the patient 2 to the external medical device 3. When the patient 2 comes near the dialysis machine 3, the IMD 1 can automatically receive the signal from the dialysis machine 3 and switch monitoring modes. This ensures that the battery life of the IMD 1 is not used up as quickly when the patient is not receiving dialysis, but provides full monitoring during a dialysis session.

In any embodiment of the first and second aspects of the invention, a wireless communication can be established between the IMD and the external medical device. This allows for the IMD to transmit data to the external source for recording, monitoring or therapy. The communication can be any type of wireless communication known in the art, including radio frequency, low energy Bluetooth, or cellular communication.

In any embodiment of the first and second aspects of the invention, the dialysis mode of monitoring of the IMD can continue for some period of time after the patient leaves the proximity of the dialysis machine. When the IMD no longer detects that the patient is near to the dialysis machine, the IMD can automatically revert back to a non-dialysis mode after some set period of time. In any embodiment of the first and second aspects of the invention, the set period of time can be between any of 1 minute to 1 day, 1 minute to 1 hour, 1 hour to 8 hours, or 6 hours to 1 day. In any embodiment of the first and second aspects of the invention, the dialysis mode of monitoring of the IMD can continue until a second trigger signal is received. The second trigger signal can be received as described herein for the first trigger signal. The second trigger signal can indicate that the dialysis session has ended, or that the patient is leaving the treatment facility.

Maintaining a high resolution mode of sensing medical parameters after a dialysis session is important to determining ways to improve the patient response to dialysis. In the time shortly after a dialysis session, a patient can experience a sustained elevated heart rate or sinus tachycardia even with no or minimal physical activity. The risk of a sinus tachycardia is increased if too much fluid was removed during a dialysis session or if fluid was removed at too high of a rate. The elevated heart rate can place the patient at risk of arrhythmia, and can negatively impact how the patient feels. By maintaining high resolution monitoring for some time after a dialysis session has occurred, the health care providers can determine if this is happening and adjust future dialysis session parameters accordingly.

Figure 2:
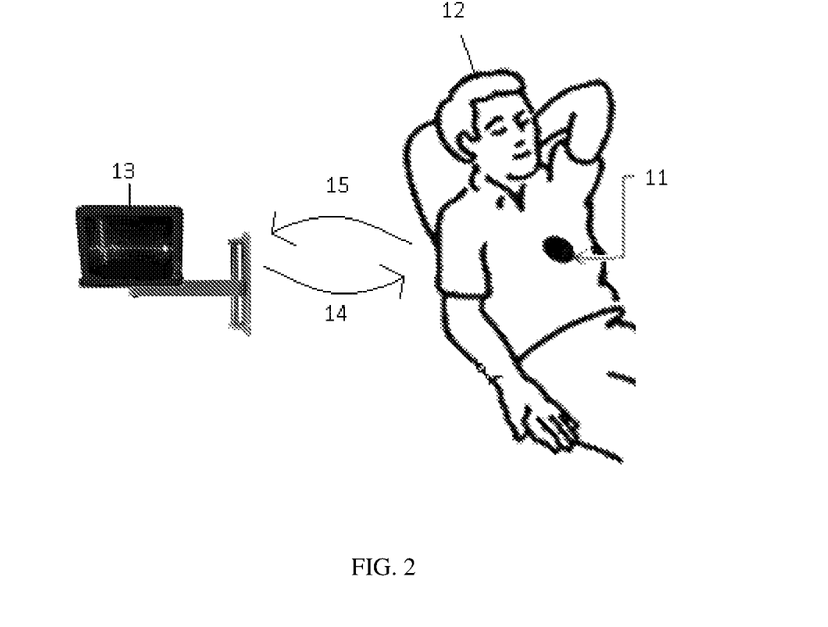
FIG. 2 is a medical monitoring system according to an embodiment, wherein the external trigger source is a medical monitor.

FIG. 2 shows another embodiment of the first and second aspects of the invention. The external medical setting in FIG. 2 is a monitor 13. When the patient 12 nears the monitor 13, the IMD 11 can automatically switch modes based on trigger signal 14. In any embodiment of the first and second aspects of the invention, the IMD 11 can switch into a transmission mode when near the monitor 13. That is, when the IMD 11 is in proximity to the monitor 13, the IMD 11 can begin transmitting the monitored medical data to the monitor 13 by signal 15, where the data can be saved or displayed. This embodiment of the first and second aspects of the invention ensures that medical data is only transmitted while the patient 12 is within the receiving range of a monitor 13 that is capable of receiving the data. Because the IMD is not transmitting information when the IMD is not within range of the monitor, the IMD conserves battery life by not using power for information transmission when there is no external medical device (EMD) to receive and display the information.

In any embodiment of the first and second aspects of the invention, the IMD can switch from a low resolution to a high resolution mode when in proximity to an external monitor. Most IMDs cannot store all of the high resolution data that the IMD is capable of sensing. For example, the memory constraints would be too high for an IMD to store ECG/EGM for the full duration of the IMD life. However, because the IMD in the embodiment of the first and second aspects of the invention shown in FIG. 2 need only measure ECG/EGM in high resolution mode when there is an external monitor capable of receiving the data, the memory constraints on the IMD are significantly reduced. Additionally, because the high resolution or real-time data is only collected during the particular window of interest, the download time for transmitting the data to a receiver will be reduced.

One skilled in the art will understand that the monitor shown in FIG. 2 need not be a stand alone monitor. The monitor can be any device capable of receiving data from the IMD and displaying or recording the data. In any embodiment of the first and second aspects of the invention, the monitor can be integral to another medical device, such as a dialysis machine. In any embodiment of the first and second aspects of the invention, the monitor may be part of a computer system. In any embodiment of the first and second aspects of the invention where the monitor is connected to a computer containing electronic medical records, the IMD can automatically switch into a mode to update the electronic medical records based on the monitored parameters.

The external medical setting that is the source of the trigger signal can be any medical device, and is not limited to a dialysis machine or monitor. In any embodiment of the first and second aspects of the invention, the external medical setting can be a scale, a blood pressure measurement system, a monitor, a nurse monitoring system, a computer having an electronic medical record, or a physiologic monitoring device. In any embodiment of the first and second aspects of the invention, the IMD can be configured to change modes based on signals that can come from multiple medical devices. For example, the same IMD may be configured to switch to a high resolution monitoring mode when near a dialysis machine, and switch to a transmission mode when near to a monitor. When the IMD is near to both a dialysis machine and a monitor, the IMD can switch into a high resolution monitoring mode and simultaneously begin to transmit the data to the monitor.

In any embodiment of the first and second aspects of the invention, the external device can be a piece of exercise equipment, such as a treadmill. The trigger can be received by the IMD when the patient steps on or near to the exercise equipment. In any embodiment of the first and second aspects of the invention, the exercise equipment can be configured to send the trigger signal when the equipment is activated and the exercise begins. Parameters such as heart rate or blood pressure are important to monitor during exercise in patients with heart disease.

In any embodiment of the first and second aspects of the invention, the external device can be a continuous positive airway pressure (CPAP) machine. Patients using CPAP machines generally have respiratory difficulty. Many CPAP users suffer from sleep apnea. These patients suffer from pauses in breathing during sleep, causing a reduction in blood oxygen. When the patient puts on the CPAP device, the trigger can be automatically sent and received by the IMD. The IMD can automatically begin to monitor blood oxygen saturation or other indications of respiratory problems while the patient sleeps. In any embodiment of the first and second aspects of the invention, the IMD can provide an alert, such as a vibration, to wake up the patient if the blood oxygen levels drop to an unsafe level. In any embodiment of the first and second aspects of the invention, the IMD can send a signal to the CPAP machine or a monitor if the blood oxygen levels drop, and the CPAP machine or monitor can provide an alarm.

In any embodiment of the first and second aspects of the invention, the medical monitoring system can be enclosed within another medical device, and need not be a stand-alone system. For example, in any embodiment of the first and second aspects of the invention, the medical monitoring system can enclosed within a dialysis system, or enclosed within a piece of an exercise equipment.

In any embodiment of the first and second aspects of the invention, the external source can interact with the IMD. For example, in any embodiment of the first and second aspects of the invention where the external source is a dialysis machine, the dialysis machine can select dialysis parameters for the patient based on the received data from the IMD. For example, the rate of ultrafiltration, the concentration of electrolytes in dialysate, dialysate pH or other dialysis parameters can be automatically determined by the dialysis machine based on the measured medical parameters of the patient. If the blood pressure of the patient drops during a dialysis session, the dialysis machine can automatically change one or more parameters in order to return the patient's blood pressure to an acceptable range. The system can stop ultrafiltration, or in any embodiment of the first and second aspects of the invention, the dialysis system can automatically add fluid to the dialysis flow loop to increase the fluid level in the patient. In any embodiment of the first and second aspects of the invention, the system can automatically determine the proper ultrafiltration rate based on patient impedance and a target impedance or treatment time. In any embodiment of the first and second aspects of the invention, the dialysis system can change the dialysate temperature based on the heart rate of the patient. In any embodiment of the first and second aspects of the invention, the IMD can be configured so that the transmission of certain data to receivers, such as can be on a dialysis machine, only occurs after the IMD receives the trigger signal. In any embodiment of the first and second aspects of the invention, the IMD can transmit to the dialysis machine a warning if the IMD senses an arrhythmia or ischemia. The IMD can cause an alert to appear on the dialysis machine, or in any embodiment of the first and second invention, cause the dialysis machine to automatically shut down. In any embodiment of the first and second aspects of the invention, the IMD can switch from a high resolution mode to a real time mode, or display an actual ECG, after the IMD senses an arrhythmia or ischemia or a heart rate increase. In any embodiment of the first or second aspects of the invention, the IMD can also store information for the patient, such as a dialysis prescription, blood borne illnesses or aversions to certain therapies. In response to a trigger signal indicating that dialysis is about to begin, the IMD can transmit the information to the therapy provider or to the dialysis machine to ensure that the therapy delivered is consistent with the needs of the patient. In any embodiment of the first or second aspects of the invention, the IMD can transmit a signal to the dialysis machine to ensure the correct materials are being used by the dialysis machine, such as sorbent cartridges or dialyzers registered to the particular patient.

Arrhythmias are medical conditions associated with the medical parameter of heart rate. In any embodiment of the first or second aspects of the invention, the IMD can adjust the mode of treatment of the medical condition based on an external signal, such as a signal indicating the start of dialysis. Dialysis machines may emit noise signals during therapy that may be detected by an IMD. As the number of patients with IMDs receiving dialysis increases, the problems occurring due to noise signals emitted by the dialysis machines may increase. As such, in any embodiment of the first or second aspects of the invention, the IMD can automatically be set to enter an alert mode, and provide an audible or visual alert when detecting fast heart rates during dialysis, instead of automatically providing therapy. In response to a trigger signal indicating that a dialysis session is beginning, or is about to begin, the IMD can switch into this alert mode. The alert mode will allow the therapy provider to prohibit a shock in response to the IMD indicating a fast heart rate if the detection of the fast heart rate is due to noise signals emitted by the dialysis machine. This can prevent unnecessary therapy being delivered to the patient. In any embodiment of the first or second aspects of the invention, the IMD can automatically enter a non-inhibited mode in response to a signal indicating the start of a dialysis session. A non-inhibited mode in an IMD causes the IMD to provide therapy independently of detection of fast heart rates. For example, a pacing treatment device can be set to deliver pacing at set time intervals. An ICD shock or similar device can be set to deliver therapy after a specific arrhythmia. A pacer dependent patient can receive the pacing therapy throughout the dialysis session automatically, so that noise signals emitted by the dialysis machine do not interfere with the therapy.

In any embodiment of the first or second aspects of the invention, the IMD can automatically change the mode of treatment of arrhythmias by adjusting arrhythmia detection parameters in response to an external trigger. Arrhythmia storing IMDs can have a set ventricular tachyarrhythmia detection rate, wherein the IMD stores arrhythmias faster than the detection rate. During a dialysis session sinus tachycardia can be expected. In any embodiment of the first and second aspects of the invention, the IMD can automatically set to a high threshold mode. That is, the arrhythmia detection rate can be set higher during the dialysis session, allowing the IMD to avoid detecting the expected sinus tachycardia, thus reducing false positive detections. In any embodiment of the first and second aspects of the invention, the IMD can be set to a low threshold mode in response to a trigger indicating the start of a dialysis session. That is, the arrhythmia detection rate can be lowered in response to the trigger indicating the start of a dialysis session. Lowering the arrhythmia detection rate during a dialysis session can help indicate to the treating technicians if the dialysis is negatively affecting the patient's heart rate. Earlier detection of arrhythmia during dialysis can allow the technicians to take appropriate action to resolve the arrhythmia early, thus preventing exacerbation of high heart rates due to the dialysis treatment and providing early warning to the therapy providers. In any embodiment of the first or second aspects of the invention, each patient may have their own reference norm for arrhythmia detection. For example, a patient prone to monomorphic VT may have an IMD with an arrhythmia detection limit of 170 bpm. Other patients, such as those with a primary arrhythmia in the absence of structural heart disease, may have a higher arrhythmia detection rate, such as 200 bpm. Based on the preferences of the health care provider, the arrhythmia detection rate can be set either higher or lower based on the external trigger. In any embodiment of the first or second aspects of the invention, the IMD can be programmed with an alternate detection rate. In response to the external trigger indicating the start of a dialysis session, the IMD can automatically change to the second detection rate. In any embodiment of the first or second aspects of the invention, the arrhythmia detection rate can be set to any other arrhythmia detection rate available in the device in response to a trigger showing that a dialysis session is starting or about to start. In any embodiment of the first and second aspects of the invention the arrhythmia detection rate can be set to between any of 90 bpm and 300 bmp, 90 bpm and 250 bpm, 100 bpm and 150 bpm, 120 bpm and 150 bpm, 150 bpm and 167 bpm, 167 bpm and 200 bpm, 175 bpm and 250 bpm, or 200 bpm to 300 bpm in response to a trigger showing that a dialysis session is starting or about to start.

In any embodiment of the first and second aspects of the invention, the therapy delivered to the patient by the IMD can also be changed based on an external trigger. For example, dialysis patients may experience slow heart rates, which can be undesirable during a dialysis session. IMDs that deliver pacing therapy work by beginning pacing therapy if the patient's heart rate drops below a set lower pacing rate. In any embodiment of the first or second aspects of the invention, a low threshold mode in an IMD can be set to automatically raise the pacing lower rate to ensure sufficient blood circulation during dialysis. This change in the lower pacing rate can occur in response to a trigger as explained herein, that shows dialysis has started, or is about to begin. The raised lower pacing rate can continue until the patient leaves the dialysis machine, for some set period after the start of dialysis, or for some set period after the patient leaves the dialysis machine. In any embodiment of the first and second aspects of the invention, the pacing rate can return to the original pacing rate based on a second trigger signal, or the pacing rate can be manually readjusted. In any embodiment of the first or second aspects of the invention, the lower pacing rate can be adjusted to between any of 30 bpm and 150 bmp, 30 bpm and 80 bpm, 50 bpm and 65 bmp, 60 bpm and 70 bpm, 65 bpm and 80 bpm, 75 bpm and 100 bpm, or 95 bpm and 150 bpm in response to a trigger showing that a dialysis session is starting or about to start.

In any embodiment of the first or second aspects of the invention, the IMD can change the mode of treating the arrhythmias by adjusting the pacing therapy outputs based on a trigger indicating that a dialysis session has started, or is about to start. Dialysis sessions can require adjusting of electrolytes, which in turn may impact pacing therapy capture during the dialysis session. In most cases, therapy outputs are either constant, adjusted due to periodic capture threshold measurements, or set to an acute phase after implant for a particular duration of time. However, due to the adjustment of electrolytes during dialysis, it may be beneficial to adjust therapy outputs in response to a trigger indicating the start of a dialysis session. For example, the IMD can increase therapy outputs by a set amount, a proportional amount, or any other amount whenever the IMD is within proximity to a dialysis machine, or in response to any other trigger indicating the start of dialysis. Each patient may have their own set value for therapy outputs, which can be changed in response to the trigger signal. In any embodiment of the first and second aspects of the invention, therapy outputs can be set to between any of 0.5 V and 8.0 V, 0.5 and 2.0 V, 1.0 V and 5.0 V, or 4.0 V and 8.0 V amplitude. In any embodiment of the first and second aspects of the invention, the pulse width of the therapy can be set to between any of 0.03 ms to 1.5 ms, 0.03 ms to 0.1 ms, 0.05 ms to 0.20 ms, 0.20 ms to 0.75 ms, 0.5 ms to 1 ms, or 0.75 ms to 1.5 ms. In any embodiment of the first or second aspects of the invention, the increased therapy outputs can be continued throughout the duration of dialysis, or for a set period of time after the dialysis session ends.

In addition to changing the frequency of measurements or transmission of data, the IMD can also change other monitoring modes. In any embodiment of the first and second aspects of the invention, the IMD can be configured to only monitor certain medical parameters after receiving the trigger. For example, parameters such as ECG/EGM morphology, heart rate, blood pressure, temperature, glucose levels and activity are generally more useful to monitor during or immediately after dialysis. Patient inactivity after a dialysis session may indicate that treatment needs to be changed. A significant change in EGM morphology can indicate a bad reaction to the dialysis, and may indicate a need to adjust electrolyte balance. A rapid change in patient temperature may indicate that the dialysis treatment is too harsh on the patient and should be adjusted. In any embodiment of the first and second invention, the IMD can be configured so that these parameters are in an "off" mode, or not measured, unless the IMD receives a trigger signal from an external source, thus saving battery life by not sensing all possible parameters at all times. When the IMD receives a trigger from the external source, the IMD can switch these parameters to an "on" mode, or begin monitoring the parameters.

Any IMD capable of monitoring a medical parameter is contemplated by the invention. Implantable ECG or electrogram sensors can be used to monitor hearth rate, heart rate variability, or to obtain an ECG. Hematocrit levels can be monitored by an implantable hematocrit sensor. Impedance or fluid status can be monitored by any implantable sensor capable of sending and receiving electrical impulses. Blood pressure, including central, peripheral, pulmonary artery, or right atrial blood pressure, can be measured by an implantable blood pressure sensor. Glucose, potassium, calcium, urea, magnesium, sodium, or other blood solutes can be monitored by any implantable chemical sensor, such as the Continuous Glucose Monitoring system by Medtronic. Activity level of a patient can be monitored by an implantable accelerometer. Respiration can be measured by a sensor capable of measuring $CO_2$ levels in the patient.

In any embodiment of the first and second aspects of the invention, the IMD can switch from a low resolution to a high resolution monitoring mode when the IMD receives the trigger signal. Low resolution monitoring provides less information, but is also less of a burden on battery life. The present invention allows for the IMD to automatically switch to a higher burden high resolution monitoring mode when a higher frequency of monitoring is necessary or desirable, such as when the patient is receiving dialysis or when the patient is within range of a monitor that can receive the data. Because changes in medical parameters can happen more quickly during and immediately after dialysis, the high resolution mode can begin when the patient is receiving dialysis, and continue for some set period of time afterward, allowing remote monitoring of the patient in the time period after dialysis.

In any embodiment of the first and second aspects of the invention, during a low resolution mode, the results of the sensing of a medical parameter can be stored in the memory of the implantable device and not transmitted to an external medical device. During the high resolution sampling, the results can be automatically transmitted to an external medical device as well as stored in the IMD, reducing the memory requirements for the IMD.

In any embodiment of the first and second aspects of the invention, the IMD can switch to a real-time mode when the IMD receives an external trigger. A real-time mode allows for sensing and transmitting of medical parameters in a constant or near constant mode, such as beat-by-beat sensing and transmitting of heart rate, blood pressure or other parameters. Sensing parameters in a real time mode provides valuable insight into the physiological response to the dialysis session. The real-time or high resolution mode can be continued for a window of time after receiving the external trigger, allowing for remote monitoring of the physiological response to dialysis after the patient leaves the dialysis machine. Real-time sensing and storage is not practical in conventional IMDs due to limitations on memory storage. However, because the real-time or high resolution mode is only active during or for a short window after dialysis according to the present invention, high levels of storage are not necessary. Table 1 shows some non-limiting exemplary embodiments of the different sensing and transmitting modes of the first and second aspects of the invention. In response to the external trigger, the IMD can switch into a real-time mode for some of the parameters listed in Table 1, a high-resolution mode for some of the parameters listed in Table 1, and a low resolution mode for some of the parameters listed in Table 1. The different modes for different parameters can be based on the external signal and the needs of the patient and health care provider. In any embodiment of the first and second aspects of the invention, the IMD can be monitoring a particular parameter, such as heart rate, in high resolution mode, but switch to real time mode if the IMD senses an event of interest, such as an arrhythmia. Additionally, in each mode the IMD can perform the function more or less often than is listed in Table 1. The "real-time," "high resolution," and "low resolution" descriptions are for descriptive purposes only, and no particular requirements are necessary to be considered in a "high resolution" or any other mode.

TABLE 1

| Function | Real-Time | High Resolution | Low Resolution |
|---|---|---|---|
| ECG | ECG or EGM Tracing | Stored every 5 minutes | Stored only if an arrhythmia occurs |
| Heart Rate | Every beat | Average based on several beats-up to 5 minutes | Average based on beats each hour or day. Histogram of rate distributions |
| Blood Pressure | Every 1-5 seconds or continuously | Every 5 minutes | Every hour to every day |
| Impedance | Every 1-5 seconds or continuously | Every 5 minutes | Every hour to every day |
| Communication with EMD | Every 1-5 seconds or continuously | Every 5 minutes | When queried or when IMD senses a receiver |
| Patient Activity Level | Every 1-5 seconds | Every 5 minutes | Every hour to every day |
| Fluid Status | Every 1-5 seconds or continuously | Every 5 minutes | Every hour to every day |
| Posture | Every 1-5 seconds or continuously | Every 5 minutes | Every hour to every day |
| Temperature | Every 1-5 seconds or continuously | Every 5 minutes | Every hour to every day |

In any embodiment of the first and second aspects of the invention, the IMD can switch from a high power consumption mode to a low power consumption mode. An increased frequency of monitoring, treating or transmitting data concerning medical parameters can cause an increase in power consumption. When the IMD is not near an EMD, reducing the frequency of certain measurements, treatments or transmissions can save on power consumption. One skilled in the art will understand that some of the functions can be reduced, to allow lower power consumption when the IMD is not near an EMD. In response to a trigger signal, the IMD can be configured to turn on or increase the frequency of some of these functions, and thus enter a high power consumption mode.

As shown in Table 1, the IMD can communicate with an EMD based on the received trigger. That is, when the IMD receives a signal from the EMD, the IMD can begin transmitting information. The IMD can be configured to optimize communications with the EMD while in high resolution or real-time mode, so as to save on battery life. The signal transmitter on the EMD can always be on. Because the EMD doesn't necessarily need a battery, and because the EMD battery may be rechargeable or replaceable if the EMD does need a battery, the EMD can constantly be transmitting the signal without the battery problems of a constantly transmitting IMD. The IMD can be configured to only transmit data while in high resolution mode. When the IMD switches back to low resolution mode, the signal transmission from the IMD to the EMD can be shut off. Thus, the collection and communication of data is optimized for battery life by only communicating the data after receiving the external trigger. In any embodiment of the first and second aspects of the invention, the same signal can cause the IMD to begin collecting data on a particular parameter, such as ECG or heart rate. Thus, in any embodiment of the first and second aspects of the invention, the IMD can only collect data while there is a receiver for transmission of the data. This will eliminate the need to store large amounts of data on the IMD, reducing memory constraints and improving efficiency and battery life. In any embodiment of the first and second aspects of the invention, the IMD can simply store the high resolution data and transmit the data to a receiver only when prompted by a different trigger signal or the user.

The trigger signal can be received based on other factors than proximity to the external medical setting. For example, if the external medical setting is a dialysis machine, the trigger can be sent to the IMD only when the machine begins therapy. In any embodiment of the first and second aspects of the invention, the trigger signal can be triggered by a user. In any embodiment of the first and second aspects of the invention, the trigger signal can be from a physical contact, such as a tapping device. In any embodiment of the first and second aspects of the invention, the trigger can be based on an algorithmic detection of certain parameters. For example, a decrease in impedance can indicate that a dialysis session has begun. In any embodiment of the first and second aspects of the invention, the trigger signal can be an external communication message. That is, a communication from outside of the system, such as from a physician or patient, can be received by the IMD and cause the IMD to change modes.

Figure 3:
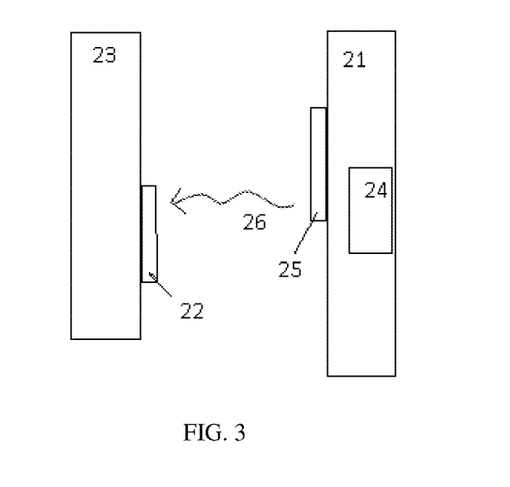
FIG. 3 is an embodiment of the trigger signal transmission using RF signals.

The trigger signal can be received by the IMD through any means known in the art. As shown in FIG. 3, in any embodiment of the first and second aspects of the invention, the trigger can be sent through a radio frequency. An RF transmitter 21 can be placed on the external medical setting, such as a dialysis machine or other external medical device. The transmitter can comprise a source 24 and an antenna 25. The source 24 generates the RF signal, which is transmitted by the antenna 25 as RF signal 26. The IMD 23, implanted in patient, can comprise an RF receiver 22. When the RF receiver 22 receives the RF signal 26 from the RF transmitter 21, the IMD can automatically switch monitoring modes as explained herein. In any embodiment of the first and second aspects of the invention, the IMD can automatically switch monitoring modes whenever the IMD is within the range of signal 26.

One skilled in the art will understand that the signals between the external source and the IMD need not be RF signals. Other examples include low energy Bluetooth, cellular, or other wireless communications systems. In any embodiment of the first and second aspects of the invention, the external source can have a magnetic field generator, and the IMD can respond to the magnetic field from the external source after detecting the magnetic field, such as with a Hall sensor.

The IMD receiver can be either passive or active. With a passive receiver, the incoming signal provides the power for the receiver to operate. The IMD can automatically detect the trigger signal whenever the trigger signal is sent. This allows for switching of the monitoring modes without the need for the patient or health care provider to cause the switch. In any embodiment of the first and second aspects of the invention, the IMD receiver can be an active receiver. The IMD's power source can provide power to the receiver, allowing for more powerful detection of the trigger signal.

In any embodiment of the first and second aspects of the invention, the medical monitoring system described herein can include a memory component. The memory component is a device capable of receiving and recording medical data from the IMD. The IMD can establish wireless communication with the memory component, and send the medical data to the memory component. The memory component can receive and record the data. In any embodiment of the first and second aspects of the invention, the memory component can be part of, or integral to, the IMD. In any embodiment of the first and second aspects of the invention, the memory component can be external, such as part of a medical monitor. In any embodiment of the first and second aspects of the invention, the memory component can be part of the external device that transmits the trigger signal. In any embodiment of the first and second aspects of the invention, the memory component can be a non-transitory recording medium.

The trigger signal, in any embodiment of the first and second aspects of the invention, can be generated by the memory component, or a device connected to the memory component. When the IMD is in proximity to the memory component, the IMD monitoring mode can switch, such that the data is sent to the memory component for recording. In any embodiment of the first and second aspects of the invention where the memory component is integral to the IMD, the memory component can store the medical data generated by the IMD and transmit the data to a monitor when the memory component is within range of the monitor.

In any embodiment of the first and second aspects of the invention, the external medical setting may be configured such that the external medical setting is always transmitting a trigger signal. This signal can be received by any IMD that close enough to the external medical setting to receive the signal. In any embodiment of the first and second aspects of the invention, the external medical setting can be configured to only transmit a signal to a particular IMD or IMDs. An example of this technology is Bluetooth pairing. The only IMDs that will receive the external medical setting trigger signal are the IMDs of the particular patients that are undergoing dialysis at the particular point in time.

In any embodiment of the first and second aspects of the invention, the IMD can be triggered to look for the external medical setting signal. The IMD can be passive until the user triggers the IMD to seek an external medical setting signal. The user can trigger the IMD to turn on a receiver or send a query signal for an external medical setting. Once the external medical setting signal is found, the IMD can switch monitoring modes as explained herein. This can be accomplished by using an external device that can cause the IMD receiver to turn on when the external device is waved over the IMD. In any embodiment of the first and second aspects of the invention, the IMD can automatically begin searching for a signal from an external medical setting after the patient enters a treatment facility. The entrance of the treatment facility can comprise a scanner that triggers the IMD to begin looking for an external medical setting signal. In any embodiment of the first and second aspects of the invention, the entrance way of the facility can comprise a magnetic field generator that can be detected by a detector, such as a Hall sensor on the IMD. In response to detecting the magnetic field, the IMD can begin looking for the external signal. In any embodiment of the first and second aspects of the invention, the IMD can be configured to begin searching for an external medical setting at a particular time, such as when the patient is scheduled for dialysis or some other medical procedure. In any embodiment of the first and second aspects of the invention, the IMD can be configured to search for an external medical setting at a set frequency, such as every 30 minutes or every hour. In any embodiment of the first and second aspects of the invention, the IMD can be configured to always be searching for the trigger signal.

In any embodiment of the first and second aspects of the invention, the hospital or treatment facility itself can be the external medical setting that serves as the source for the trigger signal. The entrance way of the facility, or particular areas within the facility, can be configured to transmit the trigger source. When a patient with an IMD enters the facility, the IMD can receive the external trigger.

Figure 4:
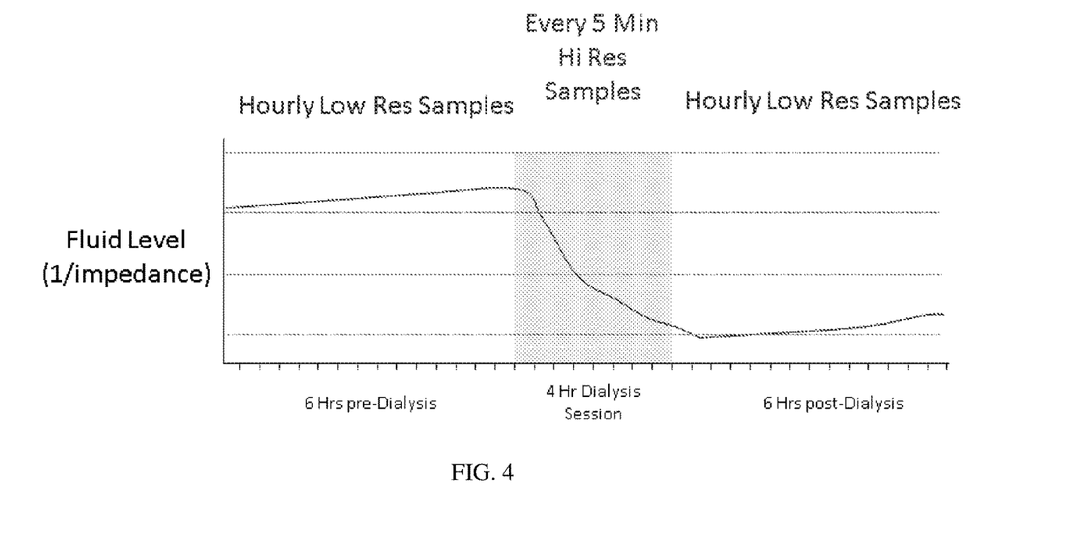
FIG. 4 is an example of a monitor display in both high resolution and low resolution modes.

FIG. 4 shows an exemplary embodiment of the data received from an IMD that switches modes in response to a signal showing that dialysis is occurring as in the first and second aspects of the invention. The chart in FIG. 4 shows the fluid level of a patient as the inverse of impedance measured by an IMD. In the time period before the dialysis session begins, the IMD is in low resolution mode, providing measurements every hour. During the dialysis session, the IMD has automatically switched to a high resolution mode, providing measurements every five minutes. After the dialysis session, the IMD automatically returns to low resolution mode, once again providing measurements of fluid level every hour. One skilled in the art will understand that the IMD can be configured to maintain a high resolution mode for a set period of time after the dialysis session. Additionally, other measurements, such as blood pressure, can be switched into high resolution mode during a dialysis session and remain in a high resolution mode for a set period of time after the dialysis session. In any embodiment of the first and second aspects of the invention, one parameter, such as impedance, can be returned to a low resolution mode immediately following or in a short window after the end of a dialysis session, while another parameter, such as blood pressure, can be maintained in high resolution mode for a longer period of time after the dialysis session.

One skilled in the art will understand that various combinations and/or modifications and variations can be made in the dialysis system depending upon the specific needs for operation. Moreover features illustrated or described as being part of an aspect of the invention can be included in the aspect of the invention, either alone or in combination.

We claim:

1. A medical monitoring system, comprising:
   an implantable medical device having one or more sensors configured to monitor data corresponding to at least one medical parameter;
   an input in electronic communication with the implantable medical device, wherein the input is configured to receive a signal corresponding to at least one trigger; and
   a dialysis machine configured to transmit the signal to the implantable medical device;
   wherein the implantable medical device is configured to perform an action of changing a mode of monitoring the at least one medical parameter or of treating a medical condition associated with the at least one medical parameter based on the signal corresponding to the at least one trigger from a first mode to a second mode;

wherein the implantable medical device is configured to switch from either a high threshold mode to a low threshold mode or from a low threshold mode to a high threshold mode in response to the at least one trigger wherein the trigger is a signal that a dialysis session is beginning or about to begin.

2. The medical monitoring system of claim 1, further comprising a monitor in wireless communication with the implantable medical device, wherein the monitor is configured to receive and display the data corresponding to the at least one monitored medical parameter.

3. The medical monitoring system of claim 1 wherein the implantable medical device is configured to transmit the data to the dialysis machine, and the dialysis machine is configured to receive the data.

4. The medical monitoring system of claim 3 wherein the dialysis machine automatically sets at least one dialysis parameter based on the received data.

5. The medical monitoring system of claim 1 further comprising a memory component in communication with the implantable medical device; wherein the implantable medical device is configured to transmit the data to the memory component; and wherein the memory component is configured to receive and record the data.

6. The medical monitoring system of claim 5 wherein the memory component is part of the implantable medical device.

7. The medical monitoring system of claim 1 wherein the at least one medical parameter is selected from the group comprising impedance, fluid status indicators, ECG or EGM, heart rate, heart rate variability, blood pressure, patient activity, glucose level, potassium level, calcium level, magnesium level, sodium level, hematocrit level, urea level, $CO_2$ level, respiration, patient posture, and patient temperature.

8. The medical monitoring system of claim 1 wherein the trigger is proximity to the dialysis machine.

9. The medical monitoring system of claim 1 wherein the medical monitoring system is enclosed within another medical device.

10. The medical monitoring system of claim 1 wherein the implantable medical device is either:
(i) configured to always be capable of detecting the trigger;
(ii) configured to be capable of detecting the trigger at a set time;
(iii) configured to be capable of detecting the trigger at a set frequency; and/or
(iv) configured such that a user can cause the implantable medical device to become capable of detecting the trigger.

11. The medical monitoring system of claim 1, wherein the mode of monitoring at least one medical parameter further comprises initiation of monitoring of a medical parameter or termination of the monitoring of a medical parameter.

12. A method, comprising the steps of:
establishing wireless communication between a dialysis machine and an implantable medical device;
receiving a trigger from the dialysis machine to the implantable medical device; and
performing an action of changing from a first data collection mode to a second data collection mode in the implantable medical device based on the trigger;
wherein the step of changing from a first data collection mode to a second data collection mode comprises changing from a high threshold mode to a low threshold mode or changing from a low threshold mode to a high threshold mode;
wherein the trigger is a signal that a dialysis session is beginning or about to begin.

13. The method of claim 12, wherein the trigger is any one of proximity to the dialysis machine, an external communication message, a user trigger, or an algorithmic trigger.

14. The method of claim 12, further comprising the step of transmitting data, control instructions, alerts, triggers, or programming between the dialysis machine and the implantable medical device via the wireless link.

15. The method of claim 14 wherein the data includes parameters for any one of impedance, fluid status indicators, ECG or EGM, heart rate, heart rate variability, blood pressure, patient activity, glucose level, potassium level, calcium level, magnesium level, sodium level, hematocrit level, urea level, $CO_2$ level, respiration, patient posture, patient temperature, and arrhythmia status.

16. The method of claim 12 further comprising performing an action of changing from the second monitoring mode to the first monitoring mode after a set period of time after receiving the trigger.

17. The method of claim 12 further comprising performing an action of changing from the second monitoring mode to the first monitoring mode after receiving a second trigger.

18. The system of claim 1, wherein the implantable medical device is an implantable pacing device.

19. The system of claim 1, wherein the first mode further comprises a high resolution or the low resolution mode and the second mode further comprises the high resolution mode or the low resolution mode.

20. The system of claim 1, wherein either the first mode or the second mode further comprises a non-inhibited mode.

* * * * *